(12) United States Patent
Schwenke

(10) Patent No.: US 8,931,349 B2
(45) Date of Patent: Jan. 13, 2015

(54) TEST APPARATUS FOR THE MECHANICAL TESTING OF COMPONENTS AND MATERIAL SAMPLES

(75) Inventor: Thorsten Schwenke, Winterthur (CH)

(73) Assignee: Thelkin AG, Winterthur (CH)

( * ) Notice: Subject to any disclaimer, the term of this patent is extended or adjusted under 35 U.S.C. 154(b) by 243 days.

(21) Appl. No.: 13/414,344

(22) Filed: Mar. 7, 2012

(65) Prior Publication Data

US 2012/0227508 A1 Sep. 13, 2012

(30) Foreign Application Priority Data

Mar. 8, 2011 (EP) ..................................... 11405230

(51) Int. Cl.
*G01N 3/00* (2006.01)
*G01N 3/08* (2006.01)

(52) U.S. Cl.
CPC .......... *G01N 3/08* (2013.01); *G01N 2203/0016* (2013.01); *G01N 2203/0032* (2013.01); *G01N 2203/0042* (2013.01); *G01N 2203/005* (2013.01)
USPC ............................................. 73/788; 73/818

(58) Field of Classification Search
CPC ............ G01N 3/08; G01N 2203/0016; G01N 2203/0032; G01N 2203/0042; G01N 2203/005
USPC ..................... 73/818, 847, 853, 726
See application file for complete search history.

(56) References Cited

U.S. PATENT DOCUMENTS

| | | | |
|---|---|---|---|
| 3,994,158 A | 11/1976 | Weinhold | |
| 5,438,863 A * | 8/1995 | Johnson | ....................... 73/54.02 |
| 5,877,432 A | 3/1999 | Hartman et al. | |
| 2004/0255698 A1* | 12/2004 | Beaman et al. | ............ 73/862.49 |

FOREIGN PATENT DOCUMENTS

| | | |
|---|---|---|
| DE | 26 56 941 A1 | 8/2003 |
| DE | 102 06 710 A1 | 8/2003 |

* cited by examiner

*Primary Examiner* — Lisa Caputo
*Assistant Examiner* — Brandi N Hopkins
(74) *Attorney, Agent, or Firm* — Birch, Stewart, Kolasch & Birch, LLP

(57) ABSTRACT

The invention relates to a test apparatus and a test method for the testing of samples by mechanical action upon the sample. The test apparatus comprises a sample region and a cylinder, which is movable in relation to the sample region, and at least two linear drives, each with a first drive part, which is fixed in place with respect to an end of the sample region, which faces it, and with a second drive part, which is movable in relation to the first drive part and is driven and which is fixed in place with respect to the cylinder. Advantageously, the movement axes of the linear drives run parallel to the longitudinal axis of the cylinder. In a preferred embodiment, a test set-up of the test apparatus has a rigid load frame.

17 Claims, 5 Drawing Sheets

TEST APPARATUS FOR THE MECHANICAL TESTING OF COMPONENTS AND MATERIAL SAMPLES

TECHNICAL FIELD

The invention relates to a test apparatus and a test method for the testing of samples (that is to say, components and material samples) by mechanical action upon the sample. The test apparatus comprises a sample region and a cylinder, which is movable in relation to the sample region, and a linear drive with a first drive part, which is fixed in place with respect to an end of the sample region which faces it, and with a second drive part, which is movable in relation to the first drive part and is driven and which is fixed in place with respect to the cylinder.

PRIOR ART

Test apparatuses for the mechanical testing of samples are used, as standard, in industry and research, for example for material testing or in load, fatigue and wear tests. Samples are understood to mean components and material samples. So that a multiplicity of mechanical movements or loads can be implemented within a useful period of time, the test apparatuses are mostly operated at a relatively high frequency, typically of the order of 10 Hz.

Conventional test apparatuses are driven partly pneumatically and, above all, also hydraulically, because these types of drive make it possible to have the requisitely high frequencies and at the same time possess sufficient force (the mechanical tests usually take place within a range of a few hundred Newton to a few thousand Newton). However, in particular, hydraulically driven test apparatuses need a large amount of space and much infrastructure, for example the large hydraulic pumps are mostly designed as a separate component and require 3-phase current terminals and also large quantities of cooling water. Moreover, the upkeep and maintenance costs are high.

For this reason, alternative types of linear drives are also readily employed, in particular servoelectric linear motors which, thanks to technological advances, have in the meantime not only sufficiently large strokes and high frequencies, but recently also have sufficient force and, in addition, are low-maintenance. For example, the patent specification U.S. Pat. No. 5,877,432 A (Univ. Dayton) describes as prior art electrodynamic vibration exciters (electrodynamic shakers) as a linear drive, the vibration exciters being based on electrodynamic linear motors. Since linear motors have large movable masses and the movable parts have to be mounted (usually by means of ball bearings), U.S. Pat. No. 5,877,432 A (Univ. Dayton) proposes to use magnetostrictive linear drives instead of vibration exciters.

U.S. Pat. No. 5,877,432 A (Univ. Dayton) also discloses, apart from various types of linear drive, the conventional set-up of the test apparatus which is used in almost all embodiments: the test apparatus has a test region and a cylinder moving in relation to the test region. The cylinder is connected to a linear drive and is driven by the latter, the longitudinal axis of the cylinder lying on the longitudinal axis of the linear drive. The test region is delimited on at least one side by an adjustable wall, mostly by an adjustable ceiling which delimits the test region upwardly and is often also designated as a crosshead. The linear drive is connected to the adjustable wall or ceiling and is thereby movable in relation to the test region, so that the cylinder can be positioned at various locations in the test region or the dimension of the test region can be modified according to the application. The adjustable wall or ceiling is in this case usually held by two girders, the girders often being designed as column-like posts, and the longitudinal axis of the linear drive lying (preferably centrally) between the girders. The linear drive and the adjustable wall can be moved along the girders, for which purpose separate and additional drives are frequently provided because of the great weight of the adjustable wall and linear drive. The adjustable wall and the linear drive can also be locked on the girders, the locks having high strength. The lock usually operates in that the adjustable wall is clamped releasably to the girders, for example by means of pneumatically operated clamping devices. Moreover, the lock is frequently monitored by means of sensors.

The disadvantage of the known test apparatuses is that they are large, have a complicated build, are susceptible to faults and are costly. Moreover, the test apparatuses are complicated to maintain and clean. Hydraulic drives need much infrastructure and a large amount of space and their upkeep involves a high outlay, linear motors with the required force are large and heavy and their cooling involves a high outlay, and alternative drives, such as, for example, magnetostrictive drives, do not satisfy all the requirements in terms of stroke, speed and force. Various auxiliary mechanisms and monitoring systems complicate the set-up.

PRESENTATION OF THE INVENTION

The object of the invention is to provide a test apparatus which belongs to the technical field mentioned in the introduction and which has a compact and simple build, enables simple and favorable maintenance and cleaning to be carried out and exhibits low susceptibility to faults.

The solution for achieving the object is defined by the features of claim 1. According to the invention, a test apparatus for the testing of samples by mechanical action upon the sample comprises a sample region and a cylinder, which is movable in relation to the sample region. Moreover, the test apparatus comprises a linear drive with a first drive part, which is fixed in place with respect to the end of the sample region which faces it, and with a second drive part, which is movable in relation to the first drive part and is driven and which is fixed in place with respect to the cylinder. However, the test apparatus also comprises at least one further linear drive with a first drive part, which is fixed in place with respect to the end of the sample region which faces it, and with a second drive part, which is movable in relation to the first drive part and is driven and which is fixed in place with respect to the cylinder. In this case, the linear drives of the test apparatus are arranged in such a way that, when a second drive part of one linear drive is in a non-deflected initial position, all the other second drive parts of the other linear drives are also in their non-deflected initial position.

Samples in this case mean mechanically fixed components and material samples, but liquids are not tested (no rheological tests). However, during testing in the test apparatus, the sample may be surrounded by a fluid and, in particular, a liquid, in some applications advantageously by a saline water solution at human body temperature, for example in order to simulate conditions such as those occurring inside a human body. The cylinder exerts pressure and/or tension upon the sample in order to test the latter; mechanical action is to be understood as meaning movement and/or compression or expansion of the sample. In this case, a transmission of force from the cylinder to the sample is ensured by at least one nonpositive connection between the sample and the cylinder and at least one nonpositive connection between the sample and a margin of the sample region. The sample region may, for example, be configured as a closed-off or open test space, or the sample region may comprise a test space or be located in such.

The at least two linear drives all serve for driving the cylinder and especially advantageously have the same functioning, type of construction and implementation. They are therefore preferably a plurality of identical motors with identical specifications. The cylinder is driven by means of a synchronous movement of the drive parts of the linear drives: all the second drive parts of the linear drives are always simultaneously in a non-deflected initial position of the drives. The non-deflected initial position in this case designates a position of the linear drive which the second drive part can assume during its movement at the least possible distance from the first drive part.

An advantage of the solution according to the invention is a more compact type of construction of the test apparatus, since a plurality of linear drives replace a single one and can therefore be smaller and be arranged more compactly. The test apparatus can also have a simpler build, because the heat generated by the linear drives can be dissipated more effectively and more simply, since the heat occurs in various linear new drives and is distributed spatially better than in the case of a single linear drive. By the load being distributed to a plurality of linear drives, each linear drive is loaded to a lesser extent, this having a positive effect upon the service life and maintenance intervals and also the frequency of breakdowns. In particular, by structurally identical linear drives being used, a stock of replacement parts can be kept small, thus saving costs. The simplified type of construction with a plurality of spatially distributed linear drives can also facilitate access to the linear drives and to other components of the test apparatus, thus simplifying maintenance and repair and also cleaning.

The term "cylinder" for transmitting the force of the linear drives to the sample is understood in the context of the invention to mean a mechanical body which extends along its "Z-axis" and has a suitable cross section (round, oval, square, polygonal) in the "X-Y plane". The body may be hollow or filled up. The cylinder preferably has a circular cross section.

As an optional feature of the invention, movement axes of the at least two linear drives run parallel to the longitudinal axis of the cylinder.

If the movement axes of the linear drives run parallel to the longitudinal axis of the cylinder, the cylinder can be coupled to the linear drives in an especially simple way. Moreover, the movement axes of all the linear drives are consequently parallel to one another, with the result that the linear drives can be arranged especially compactly in relation to one another and also in relation to the cylinder. Furthermore, the drive of the cylinder is especially efficient when it is moved in a direction parallel to the working directions of all the linear drives. A great advantage of a parallel arrangement of the linear drives and of the cylinder is also high rotational rigidity of the overall set-up.

Alternatively, the movement axes of the linear drives may also not run parallel to the longitudinal axis of the cylinder and, in particular, do not even have to run parallel to one another.

As a further optional feature of the invention, the second drive parts and the cylinder are connected to one another by means of at least one bridge, in particular the cylinder being connected rigidly to the bridge.

A bridge is a very simple and stable coupling of various parts and is therefore correspondingly beneficial and permanent. To avoid states of constraint arising from too many rigid connections and risks thereby occurring, such as, for example, tilting or wedging of movable parts, the generation of stresses within the structure or the slowing or blocking of movements, advantageously not all the second drive parts and/or the cylinder are connected rigidly to the at least one bridge. A connection of all the second drive parts and of the cylinder by means of a single bridge is especially advantageous, the cylinder being connected rigidly to the bridge, but the second drive parts all having a connection to the bridge which, on the one hand, transmits the drive force according to requirements and, on the other hand, possesses degrees of freedom for preventing states of constraint (for example, dampers, joints, play, flexibility as a result of rotation and/or bending, etc.).

Alternatively, the second drive parts and the cylinder may also be coupled to one another otherwise than by a bridge, for example by joints, levers, chains, toothed belts and/or other mechanical means.

As an optional feature of the invention, electromagnetic motors, in particular servoelectric linear motors, are used as the linear drive.

Electromagnetic motors and, in particular, servoelectric linear motors have the advantage that they have a compact external mass and can be integrated directly into the test apparatus. Moreover, electromagnetic motors do not require major infrastructure—a simple current terminal is sufficient (in contrast, for example, to hydraulic systems which presuppose external water cooling circuits and 3-phase current terminals). Through the use of a plurality of linear drives, the generation of heat is also distributed spatially, and the heat can be transported away relatively simply.

Servoelectric linear motors have, in a first drive part, actuator coils with windings having three separate phases and, as a second drive part, an actuator piston composed of layered permanent magnets with alternating polarity. Typically, these servoelectric linear motors have three cascade control loops having this sequence (in decreasing priority): control in terms of position, speed and coil current. However, single-stage or two-stage control loops may also be used. Position determination may take place absolutely or relatively.

Alternatively, the linear drive may, for example, also be operated in another electromechanical way, such as, for example, by means of piezoelectric, electrostatic, magnetostrictive or thermoelectric effects, or else by pneumatics or hydraulics or by mechanical drives, such as, for example, roller threads or threaded rods.

Furthermore, the linear drives on the test apparatus may optionally be controlled individually by drive controls separate from one another, the drive controls being controlled by a common automatic control system.

Separate drive controls of the linear drives have the advantage that the individual linear drives can be controlled individually and, in particular, can interact with control loops and sensors, if present. In this case, a common automatic control system controls the drive controls of the individual linear drives, so that synchronization of the linear drive movements is carried out on one level of the drive controls by the automatic control system and the drive controls carry out the actual linear drive movements on a lower level. Complicated regulating and monitoring mechanisms of all the linear drives can thereby be simultaneously avoided.

Alternatively, the linear drives may all be operated by means of the same drive control or, for example, also in pairs or in groups of a plurality of linear drives by means of one or more drive controls (the number of linear drives per group may in this case vary and also comprise groups of different size).

As a further optional feature of the invention, the longitudinal axis of the cylinder forms a rotational axis of symmetry for the longitudinal axes of the linear drives. In this case, in particular, in at least one section through the test apparatus, running perpendicularly to the longitudinal axis of the cylinder, a straight line connecting all the points of penetration of the longitudinal axes of the linear drives through the sectional plane or an area spanning all the points of penetration of the longitudinal axes of the linear drives through the sectional plane has a geometric center of gravity which lies on a geometric center of gravity of the sectional area of the sample region through the sectional plane. In the case of 3 or 4 drives, the points of penetration are either on a line (that is to say, arranged linearly), and the geometric center of gravity lies there in the middle of the line. Or there are 3 or 4 points of penetration distributed over an area, that is to say a triangle or square, when an area spanning the points of penetration are observed. This area should be rotationally symmetrical with respect to the point of penetration of the cylinder longitudinal axis. And the center of gravity of the sectional area of the test apparatus should then be at the center of gravity of this triangle or square, so that the linear drives are arranged symmetrically with respect to the sample region.

By the longitudinal axes of the linear drives being arranged rotationally symmetrically about the longitudinal axis of the cylinder, it is possible to have an especially compact and robust type of construction of the drive mechanism, this type of construction being as free of distortion and of tilting as possible on account of a uniform force distribution. Moreover, the entire test apparatus can have a spatially compact build when the drive mechanism is arranged symmetrically with respect to the sample region.

Alternatively, the longitudinal axes of the linear drives may also be arranged asymmetrically about the longitudinal axis of the cylinder, and the geometric center of gravity of the line or area which comprises all the points of penetration of the longitudinal axes of the linear drives in the sectional plane also does not have to lie on the geometric center of gravity of the sectional area of the sample region in this sectional plane.

In a further optional feature of the invention, bearings for the cylinder are formed in a separate bearing module, the bearing module being configured as an exchangeable part of a load frame (for example, in that it is fastened by means of a non-destructively releasable screw or plug connection instead of by an only destructively releasable welded joint).

At least one and preferably two bearings for the cylinder are combined in a separate bearing module which can be built into the load frame and demounted from it relatively simply and quickly. Any replacement of bearings is thereby simplified and speeded up, and therefore low-friction and distortion-resistant mounting of the cylinder becomes possible. The bearings guide the cylinder and can advantageously be designed to be overdimensioned for the purpose of absorbing high lateral forces possibly occurring, overdimensioned meaning enlargement which lies markedly above the customary safety margins. The safety margins of test systems are usually around a factor of 10 (for example, a bearing for the cylinder is usually designed for a force higher by a factor of 10 than the calculated maximum applied force). Overdimensioned means here factors between the calculated maximum applied force and the design (that is to say, maximum load-bearing capacity) of at least a factor of 50 and, in particular, of at least a factor of 100. On account of the forces employed and the high working frequency, the bearings must be considered as wearing parts which have to be replaced at regular intervals. An uncomplicated exchange of wearing parts is advantageous for maintenance and repair and also for cleaning.

The at least one bearing may, however, also be built directly on the load frame or be formed in the latter, without being integrated into a bearing module. Bearings without simple exchange may also be provided, in which case, as regards a plurality of bearings, combinations of bearings exchangeable simply and not simply and of bearings integrated in modules and not integrated in modules are also possible.

As a further optional feature, the cylinder is configured as a hollow profile and, in particular, as a circular-cylindrical hollow profile.

If the cylinder has a hollow profile, it can have a relatively low weight, while preserving high mechanical rigidity, thus resulting in a low moved mass and therefore saving drive energy, minimizing vibrations and entailing less outlay in structural terms. The cylinder is especially advantageously configured as a circular-cylindrical hollow profile, so that the cylinder can be guided in a simple way by annular bearings. By its form of construction as a hollow profile, the cylinder can also be configured in a very simple way so as to be overdimensioned, so that torsional forces can be minimized.

Alternatively, the cylinder may also be composed of one solid piece, have different profiles at different locations and/or be composed of different parts with different cross sections and of different materials (separately and/or in combination with one another). However, the hollow profile may also be filled up.

Furthermore, the test apparatus may optionally comprise at least one measurement system which is coupled to the cylinder, in particular one or more of the following measurement systems: strain gages, position transmitters (incremental or continuous), force sensors for determining pressure force.

For simple and efficient monitoring of the mechanical action upon the sample in-situ and in real time and for controlling and regulating the linear drives, it is greatly advantageous to couple the cylinder to at least one measurement system. To determine the force exerted upon the body, for example, at least one strain gage can measure the compression of the cylinder, but preferably four strain gages which are mounted most especially advantageously inside a hollow profile where the strain gages and also the cables and, if appropriate, electronic elements are protected from external effects. However, force sensors for measuring a pressure applied between pressure plates of the force sensor which lie transversely to the longitudinal axis of the cylinder (for example, by capacitive, inductive, piezoresistive or piezoelectric sensors) may also be fastened in or on the cylinder, in order to measure the mechanical pressure upon the sample. Basically, the pressure plates or the force sensors may be arranged between the sample and cylinder and/or between the sample and a margin of the sample region.

By position determination, conclusions can be drawn as to the deformation of the sample, which, in turn, makes it possible to deduce the force exerted upon the sample. The test apparatus may be equipped, for example, with an incremental or continuous position measurement system. In this case, typically, a marked strip fastened to the cylinder moves in relation to a sensor fastened to the remaining test apparatus, with the result that the position of the cylinder can be measured with an accuracy of one micrometer or less.

Alternatively, the cylinder may also be operated without measurement systems coupled to it. The movement of the cylinder either may be controlled entirely without cylinder feedback or information regarding the force exerted upon the sample may also be obtained in a way other than that described above. For example, in the case of linear motors, the force exerted upon the sample can be deduced from the current applied to the linear drives. Or the sample itself is detected by means of sensor systems (for example, the above-mentioned measurement systems may also be coupled to the sample: strain gages and/or pressure plates on or around the sample, marked strips and sensors or else other visual detection methods directly on the sample, etc.).

As a further optional feature, the cylinder and/or a margin of the sample region have/has quick-action fastenings.

Quick-action fastening designates in the context of this application device parts which can be connected nonpositively to one another and separated from one another without complicated or repetitive movement. Typical quick-action fastenings are, for example, quick-connect fastenings, bayonet fastenings, snap-fastenings, touch-and-close fastenings and fastenings which are held together by magnetic forces or springs, rubber bands, hooks, eyes or loops. Further typical quick-action fastenings can be implemented, for example, by sliding or turning, latching or wedging together. In particular, quick-action fastenings can be fixed and released without tools, that is to say purely manually. Fastenings with rotations of more than one complete revolution (such as, for example, most commercially available screws) are not quick-action fastenings within the meaning of the invention.

Quick-action fastenings make it possible to fasten further elements to the cylinder and/or to a margin of the sample region in order to adapt the cylinder and/or the sample region simply and quickly to the respective task. In this case, it is necessary to ensure that the quick-action fastenings conform to the requirements of the respective task in terms of the strength of the fastening (especially with regard to movability of the connected parts and to a minimum necessary holding force of the fastening). The elements to be fastened may be a multiplicity of various elements having different tasks; the elements may serve, for example, for fastening the sample, may be systems or parts of systems for the detection of measurement variables or may, for example, also place the sample into a desired environment or under the desired conditions (for example, into a liquid bath, into a heat, cold and/or pressure chamber, etc.). Measurement is thereby facilitated considerably, since the sample can be positioned simply and quickly in the sample region and the sample can be placed simply and quickly under the desired conditions and observed.

Alternatively, quick-action fastenings may even be dispensed with and conventional fastening methods may be adopted, in particular screw connections, especially advantageously via prefabricated grooves, holes and/or threaded holes. In this case, other fastening and/or centering elements may also be envisaged which may be arranged, as desired, on the cylinder and/or on a margin of the sample region and, in particular, on a baseplate.

As a further optional feature of the invention, an adapter is provided, the cylinder or the adapter or both having fastening mechanisms in order to connect the cylinder and adapter nonpositively to one another. Likewise or alternatively to this, inserts are optionally provided which can be fastened to a margin of the sample region of the test apparatus and, in particular, to a baseplate of a load frame at least partially surrounding the sample region and serve for positioning the sample in the sample region.

The adapter serves for a lengthening of the cylinder which makes it possible to adapt the length of the cylinder to requirements demanded by various tasks and which takes place in an uncomplicated way by virtue of the fastening mechanism. An adapter is especially advantageous which has the same profile as the cylinder and, owing to the corresponding size, a high torsional strength of the cylinder, together with the adapter. Instead of adapting the length of the cylinder, or else even in addition to this, the margin of the sample region may be modified in such a way that the sample can be brought nearer to the cylinder. For this purpose, for example, inserts may be used which make it possible to adapt the sample region in a simple way and which can extend or raise the margin of a sample region (and, in particular, the baseplate) in the manner of a pedestal, in order to facilitate positioning of the sample.

Alternatively, an adapter and/or inserts may be dispensed with, or else only the fastening mechanisms may be dispensed with.

Optionally, the test apparatus may have a rigid and nonadjustable load frame, the load frame at least partially surrounding the sample region.

A rigid load frame which at least partially surrounds the sample region makes it possible to have a simple and also distortion-resistant structure. Moreover, in comparison with conventional attachments, additional drives for moving the cylinder drives are just as unnecessary as complicated fastening mechanisms and/or sensors.

Alternatively, a rigid load frame may also be dispensed with and the margin of the sample region may be configured adjustably and the first drive parts movably in relation to the sample region.

Optionally, the linear drives are mounted laterally on the load frame, specifically on the outside with respect to the sample region.

A further option is to provide two bearing modules for the vertically movable cylinder. Both bearing modules can be fixed in the rigid load frame.

As a further optional feature of the invention, the test apparatus is protected against damage and soiling by at least one housing, the at least one housing and, in particular, a housing in the vicinity of the sample region or delimiting the latter being designed to be at least partially dust-proof and water-tight.

At least one housing, which comprises at least part of the test apparatus, allows simple cleaning and protects the corresponding parts of the test apparatus and especially advantageously the margin of the sample region from damage caused, for example, by special sample conditions, such as, for example, liquid and/or corrosive surroundings. Moreover, appropriately well-encapsulated housings can make the test apparatus compatible with clean rooms, that is to say the test apparatus conforms to clean room standards after thorough cleaning of the surface of the housing.

Alternatively, dust-proofing, water-tightness and/or clean room compatibility or, entirely, housings may also be dispensed with.

As a further optional feature of the invention, the test apparatus comprises a test set-up in the form of a desk model.

Depending on the embodiment of the invention, the constituents of the test apparatus may be combined in one or more units or attachments. A unit designated as a test set-up comprises at least the sample region, linear drives and cylinder of the test apparatus. However, for example, at least part of the control and regulation electronics may be combined in a control unit separate from the test set-up, and a computer separate from the test set-up and the control unit may serve for operation. However, separation of the control unit and test set-up is not mandatory, and therefore the test set-up may also comprise the entire control or regulation electronics. The computer, too, may be provided as an independent appliance or be combined with other constituents of the test apparatus.

The test set-up is advantageously designed as a desk model which can be used on commercially available laboratory benches. Neither size nor weight or other factors (such as, for example, screenings, such as heat shields or, for example, vibration damping) on the part of the test set-up in this case place unusual demands upon the laboratory desk. The test set-up is therefore smaller than a cube with an edge length of 1.5 meters and does not overshoot a weight of 150 kg. A test set-up in the form of a desk model saves space and allows an ergonomic type of operation and also use of the test apparatus, without unusual demands being placed upon its location.

Alternatively, the test apparatus may also be configured otherwise than with a test set-up in the form of a desk model, in particular with a test set-up which is placed on the ground.

The invention also embraces a test method for the testing of samples by mechanical action upon the sample, which comprises the following steps: at least unidirectionally nonpositive connection of the sample to a margin of the sample region and at least unidirectionally nonpositive connection of the sample to a cylinder, the deflection of the cylinder in relation to the sample region taking place as a result of the simultaneous movement of at least two linear drives.

By the at least unidirectionally nonpositive connection of the sample to a margin of the sample region and to the cylinder, force can be exerted mechanically upon the sample, the cylinder taking place as a result of the simultaneous movement of at least two linear drives. The advantage of using a plurality of linear drives is that the load is distributed to a plurality of drives and each individual drive is thereby subjected to lower load. Moreover, with a plurality of motors being used, redundancy can be achieved, and one large moved mass is divided into a plurality of small moved masses, thus simplifying the drives of the total mass and being advantageous in safety and operational terms.

In this case, it is especially advantageous if the movement of the linear drives takes place at any time in the same direction and, in particular, also at any time in the same direction as the movement of the cylinder. All the movements can thus be linked to one another in a relatively simple way.

Further, it is also advantageous to check the movement of the cylinder (for example, by measuring the force acting upon the sample, the position of the cylinder or of the drive parts, the supply of energy by the drive controls or the like) and, where appropriate, to readjust the said movement, in particular by feedback.

And it is most especially advantageous if, in order to make the at least unidirectionally nonpositive connection of the sample and the margin of the sample region or the cylinder, the linear drives are not moved in relation to the sample region, but instead the cylinder is lengthened or shortened and/or inserts are fastened to the margin of the sample region.

Further advantageous embodiments and feature combinations of the invention may be gathered from the following detailed description and from the entirety of the patent claims.

BRIEF DESCRIPTION OF THE DRAWINGS

In the drawings used for explaining the exemplary embodiment.

Identical parts are basically given the same reference symbols in the figures. The illustrations in a front view have the same orientation as the illustration plane or the paper: the elements illustrated in the figures which lie in the direction of the lower or the upper edge of the paper lie respectively at the bottom or at the top. The same applies to the sides: the elements illustrated in the figures which lie in the direction of the left-hand or right-hand edge of the paper lie on the left or on the right respectively.

WAYS OF IMPLEMENTING THE INVENTION

Figure 1:
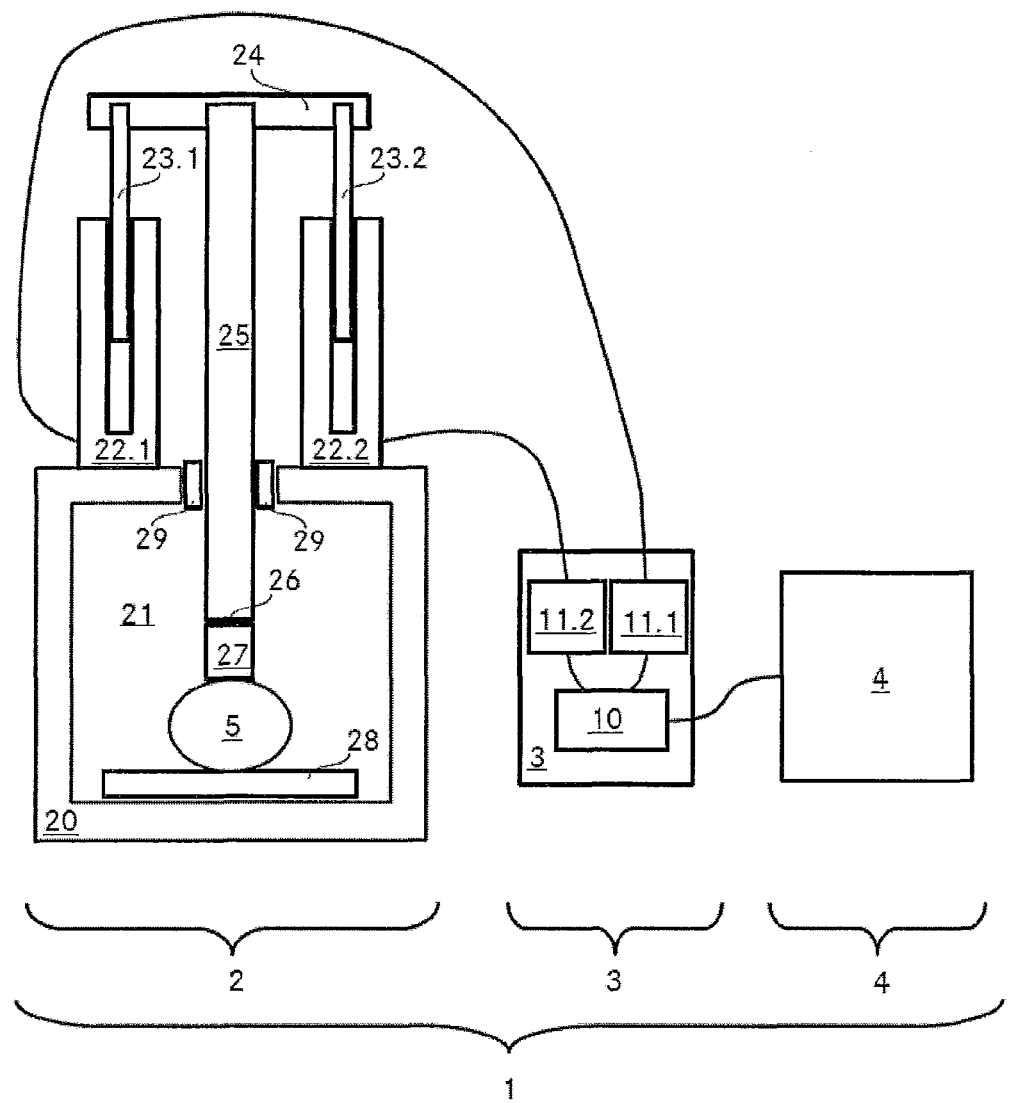
FIG. 1 shows a diagrammatic set-up of a test apparatus according to the invention in a front view.

FIG. 1 illustrates a front view of a diagrammatic set-up of a test apparatus 1 according to the invention. In this preferred embodiment, the test apparatus 1 is in the form of three separate units: a test set-up 2, a control unit 3 and a computer 4. The computer 4 is a commercially available computer which communicates with the control unit 3 via a computer program and, in particular, via a program written specifically for the test apparatus 1. The computer program serves for controlling, regulating and monitoring the test apparatus 1, for the mechanical testing of a sample 5 and for the presentation and evaluation of results of this mechanical test. For this purpose, the computer program communicates with an automatic control system 10 of the control unit 3, the automatic control system 10 interacting in turn with two drive controls 11.1 and 11.2. The drive controls 11.1 and 11.2 in each case control a linear drive of the test set-up 2.

The test set-up 2 comprises a rigid load frame 20 which at least partially surrounds a sample region 21. Two linear drives with parallel longitudinal axes comprise first drive parts 22.1 and 22.2 and second drive parts 23.1 and 23.2, the first drive parts 22.1 and 22.2 being connected firmly to the load frame 20. The second drive parts 23.1 and 23.2, by contrast, can move downward and upward in relation to the sample region 21, the second drive parts 23.1 and 23.2 being connected to one another by means of a bridge 24 at their upper end remote from the sample region 21. Also fastened to the bridge 24 is a cylinder 25, the longitudinal axis of which is parallel to the longitudinal axes of the linear drives. The cylinder 25 extends from the bridge through the load frame 20 downward into the sample region 21 and ends there in a cylinder end face 26. Following the cylinder end face 26, an adapter 27 is fastened nonpositively to the cylinder 25, the adapter 27 prolonging the cylinder 25 downward in the direction of the sample 5 and being in nonpositive contact with the sample 5. The sample 5 is also in nonpositive contact with an insert 28, the insert 28 being connected nonpositively to the load frame 20 at a lower end, opposite the cylinder, of the sample region 21. The cylinder 25 is guided in its movement by a bearing module 29 which is part of the load frame 20, comprises two bearings and mounts the cylinder 25 with low friction and in a distortion-resistant manner. In the present embodiment, the test system is designed for axial forces of up to 2.5 kN. In test machine building, a transverse force amounting to as much as 10% of the axial force is normally assumed, that is to say, here, up to 250 N. A bearing has a static load-bearing coefficient of more than 35 kN, that is to say is overdimensioned by a factor of 140.

Figure 2:
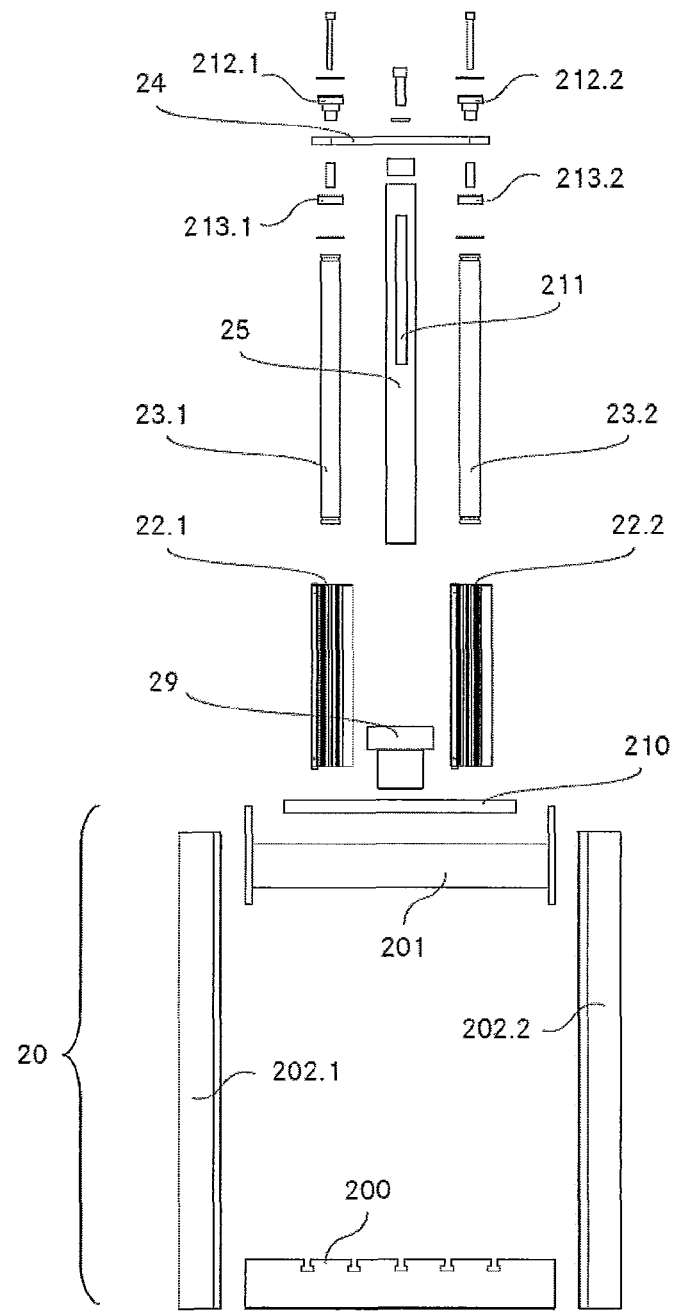
FIG. 2 shows an exploded drawing of a test set-up according to the invention in a front view.

FIG. 2 shows an exploded drawing of a test set-up according to the invention in a front view. The load frame 20 is composed of a baseplate 200, of a top plate 201 and of two side walls 202.1 and 202.2. The side walls 202.1 and 202.2 are in this case fastened to the left-hand and the right-hand side of the baseplate 200 and of the top plate 201. Above the top plate 201 lies a drive bed plate 210, on which the first drive parts 22.1 and 22.2 are fastened from above. In the mounted state, the bearing module 29 projects through the drive bed plate 210 into the top plate 201 and guides the cylinder 25 with low friction and in a distortion-resistant manner. The cylinder 25 is designed as a hollow cylinder with an annular cross section and has an outside diameter of 40 mm, the bearings of the bearing module 29 having correspondingly large dimensioning. The cylinder 25 is about three quarters as long as the side walls 202.1 and 202.2 are high and has a stroke of typically a maximum of 100 mm. Fastened to the cylinder 25 is a marked strip 211 which, in interaction with a sensor, enables an absolute position determination of the cylinder 25 accurate to 0.5 micrometers to be carried out. The marked strip 211 consists of gold and has horizontally lined patterning.

The cylinder 25 lies in the middle of the two second drive parts 23.1 and 23.2 and has a longitudinal axis parallel to their longitudinal axes. The second drive parts 23.1 and 23.2 are about five sixths as long as the cylinder 25. The cylinder 25 and the second drive parts 23.1 and 23.2 are connected to one another at their upper ends via a common horizontal bridge 24. In this case, the cylinder 25 is screwed firmly to the bridge 24, whereas the second drive parts 23.1 and 23.2 are screwed to the bridge 24 by means of upper and lower rubber buffers 212.1, 212.2 and 213.1, 213.2 so as to be mechanically decoupled to an extent such that states of constraint in the structure are not generated by too many load-bearing and rigid guides and that no internal stresses can cause wedging of the structure. The only load-bearing bearings are located in the bearing module 29.

Figure 3:
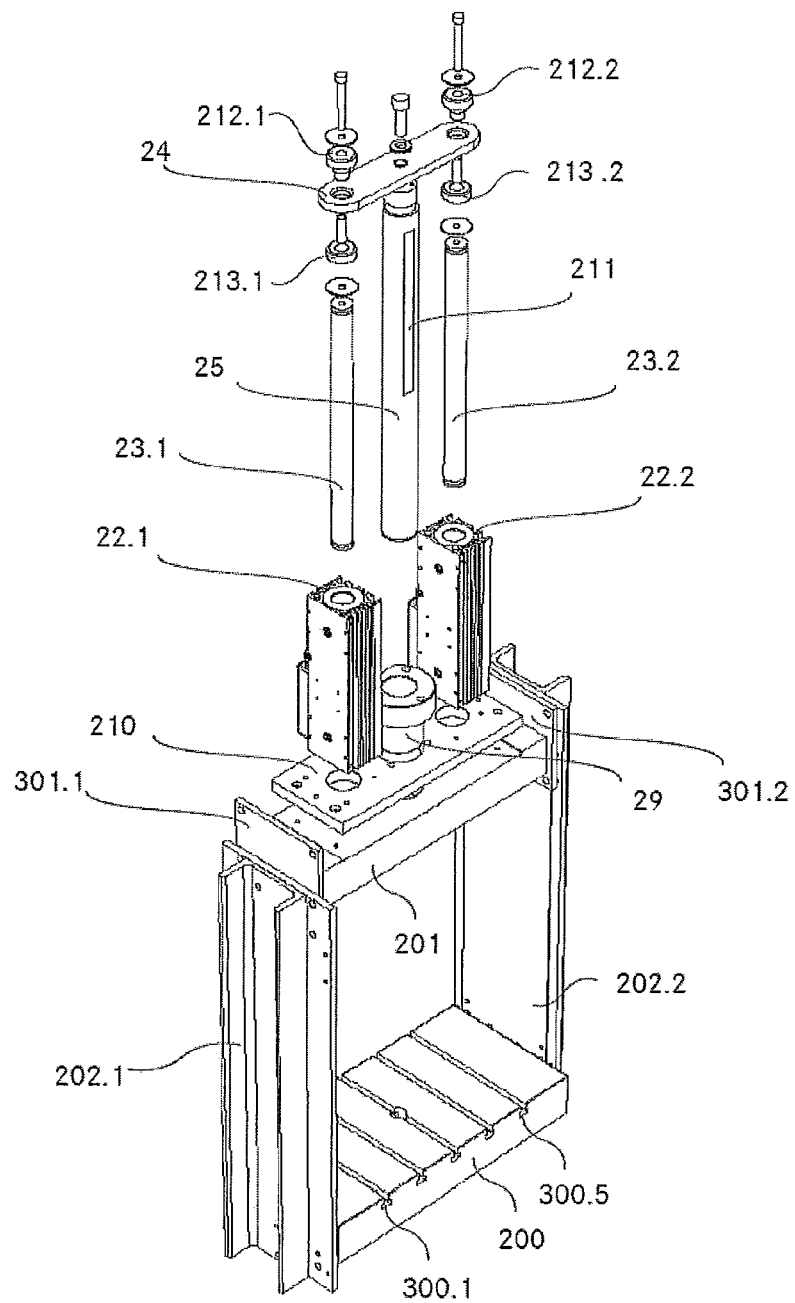
FIG. 3 shows the exploded drawing as in FIG. 2, illustrated in perspective.

FIG. 3 shows the same test set-up in an exploded drawing as in FIG. 2, but in a perspective illustration. What can be seen clearly in this illustration are grooves 300.1 to 300.5 on the top of the baseplate 200 which serve for the fastening of samples 5, sample holders or inserts 28. The baseplate 200 has a rectangular horizontal projection in which the short side is about half as long as the long side, and is about one quarter as high as the short side is long. The top plate 201 has about the same dimensions as the baseplate 200, but on the left-hand and right-hand narrow side has fastening plates 301.1 and 301.2 for fastening to the side walls 202.1 and 202.2. The side walls 202.1 and 202.2 are about twice as high as the long side of the baseplate 200 and are composed of a plate pointing toward the sample region and of a U-profile which is fastened thereto on the side remote from the sample region and the legs of which point away from the sample region. The U-profile gives the side walls 202.1 and 202.2 high stability.

Figure 4:
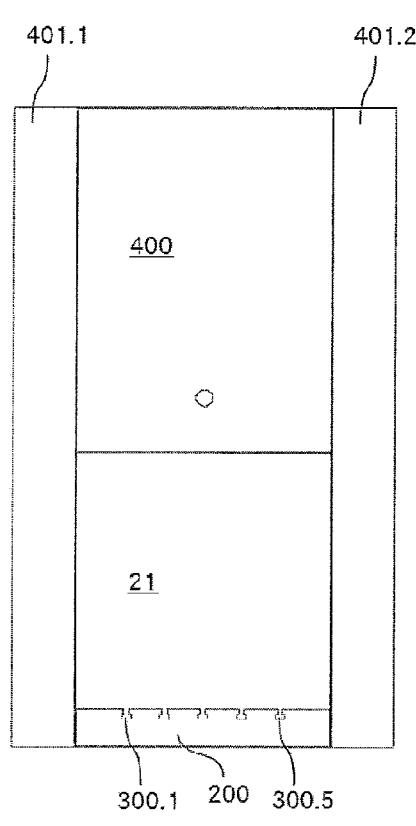
FIG. 4 shows a front view of the test set-up according to the invention from FIG. 2 with a housing.

FIG. 4 illustrates the same test set-up as in FIG. 2, likewise in a front view, but in the assembled state and provided with a housing. The baseplate 200 and the fastening grooves 300.1-300.5 are arranged so as to be freely accessible at the lower end of the test set-up from the sample region 21 open toward the front and the rear, whereas the largest part of the remaining test set-up is covered by a multipart housing. The multipart housing is designed in such a way that, during all movements according to the invention of the cylinder 25, no parts of the test set-up leave a region spanned by the housing and the sample region 21. The cylinder 25 is in its position deflected upward to the maximum, with the result that the lower end of the cylinder does not project below the lower end of the top plate and therefore cannot be seen in FIG. 4.

On the left-hand and right-hand side, a left side housing 401.1 and a right side housing 401.2 surround the test set-up over its entire height. The side housings 401.1-401.2 at least partially surround, on the lateral outsides of the test set-up, the side walls 202.1-202.2 of the load frame and all the components of the test set-up lying above it, up to at least the maximum deflection of the cylinder 25 and of all the parts connected to it. The upper part, lying above the sample region 21, of the test set-up is covered between the side housings 401.1-401.2 toward the front by a front housing plate 400. The front housing plate 400 is designed as a planar plate which is delimited laterally by the side housings 401.1-401.2 and which extends from the lower end of the top plate 201 as far as the upper end of the test set-up. Located in a corresponding position on the rear side of the test set-up is a rear housing plate which is designed identically to the front housing plate 400 (cannot be seen in FIG. 4).

Figure 5:
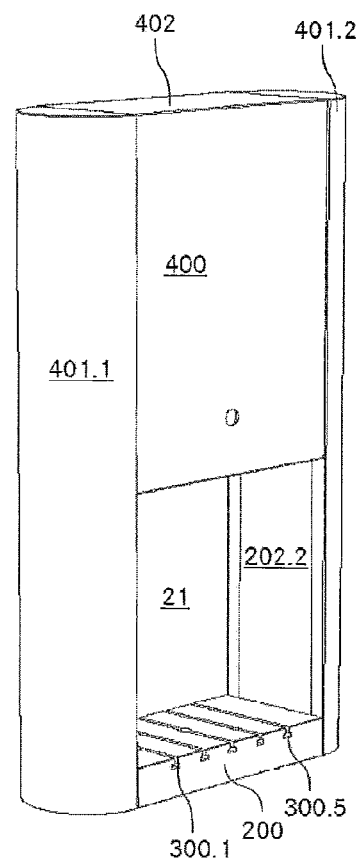
FIG. 5 shows a perspective illustration of the test set-up according to the invention from FIG. 4.

A perspective view of the test set-up illustrated in FIG. 4 is depicted in FIG. 5. As can be seen clearly, the baseplate 200 having the fastening grooves 300.1-300.5 is arranged at the lower end of the test set-up and is surrounded on the lateral outsides of the test set-up by the side housings 401.1-401.2. The side housings 401.1-401.2, shaped so as to be outwardly semicircular and vertically straight, as seen in a horizontal section, surround the side walls 202.1-202.2 toward the outside of the test set-up, but not toward the sample region 21. The side housings 401.1-401.2 are closed off at their upper and lower end by horizontal surfaces. Between the upper two of these horizontal surfaces of the side housings 401.1-401.2, a housing cover 402 closes off the test set-up upwardly. The housing cover 402 is designed as a planar plate which is delimited laterally by the upper horizontal surfaces of the side housings 401.1-401.2 and which adjoins the front housing plate 400 and rear housing plate with a form fit at the front and rear.

The side housings 401.1-401.2, the front housing plate 400 and the rear housing plate and the housing cover 402 together form a closed housing jacket which closes off the test set-up outwardly in a dust-proof and water-tight manner and which thereby prevents the test set-up from being damaged and soiled and also injuries to persons standing around it and makes it possible to clean the test set-up and sample region 21 in a simple way.

The embodiment of the test apparatus illustrated in FIGS. 2-5 and designed as a desk model is 1.2 m high, 0.6 in wide and 0.4 m deep and does not overshoot a weight of 80 kg. The desk model can be fastened to the desk on which it stands. For this purpose, threaded holes are located on the underside (lying on the desk) of the test apparatus.

Figure 6:
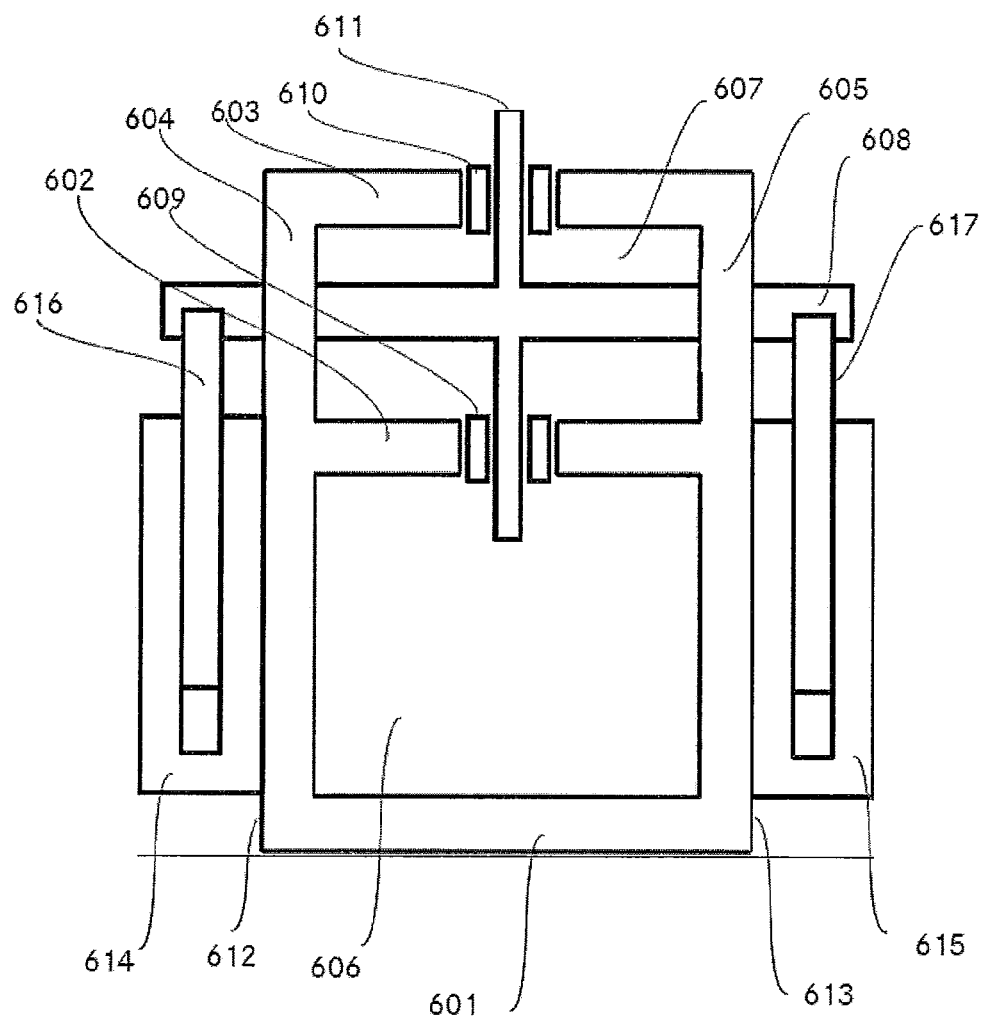
FIG. 6 shows a diagrammatic illustration of a further embodiment of the invention.

The design variant shown in FIG. 6 differs from the variants described further above, above all, in that the linear drives are mounted laterally on the rigid load frame and in that the rod which transmits the force of the linear drives to the sample is guided in two bearings.

The rigid load frame is formed by a lower beam 601, a middle beam 602 and an upper beam 603 and by two lateral posts 604 and 605. The beams 601-603 running horizontally and parallel to one another are fixed to the lateral posts 604, 605 at different heights. Between the lowermost beam 601 and the middle beam 602, a sample space 606 is formed, which, for example, is as wide as it is high. The workpiece sample to be tested is mounted in the sample region or sample space 606.

Between the middle beam 602 and the uppermost beam 603, a free space 607 is formed, in which a cross member 608 is arranged so as to be vertically movable. The free space 607 preferably has, for example, a similar height to the sample space 606.

The cross member 608 extends laterally beyond the posts 604, 605. It may project through orifices in the posts 604, 605 and, if required, also be guided by them. Alternatively, the cross member 608 may run laterally past the posts 604, 605.

A bearing 609, 610 is provided in each case in the middle of the middle and of the upper beam 602, 603. A plunger 611 is guided, so as to be movable parallel to the posts 604, 605, in these two bearings 609, 610 aligned with one another. The plunger 611 may be a cylinder overdimensioned in cross section or may also be another rod. The plunger 611 is connected to the cross member 608, so that the two parts mentioned are coupled motionally to one another.

A part of, for example, the cylinders 614, 615 of the two linear drives is mounted on each of the two outsides 612, 613 of the posts 604, 605. The pistons 616, 617 are guided in the cylinders 614, 615, project upwardly out of the cylinders 614, 615 and are connected to the two ends of the cross member 608. The two linear drives may be designed and activated in the same way as described in the preceding exemplary embodiments.

In summary, it is to be noted that the above-described embodiments do not restrict the invention and a multiplicity of other embodiments and sizes of test apparatuses within the meaning of the invention are also embraced explicitly by the invention. Thus, for example, the test set-up, control unit and computer may be combined as separate units, but also in any combinations with one another in different units. A computer may even be dispensed with if the automatic control system is equipped with other interaction means. The linear drives may be controlled both individually and in groups via one or more drive controls. More than one automatic control system may also be present, particularly when a large number of measurement systems monitor the progress of the mechanical test. The number of linear drives may amount to 2, 3, 4, 5 or more, and their arrangement may lie in one plane or be distributed spatially (in the case of 3 linear drives, for example, arranged at the corners of an equilateral triangle with longitudinal axes of the linear drives standing perpendicularly to the triangle).

The load frame may be configured both rigidly and so as to be vertically adjustable, and the longitudinal axis of the cylinder may have a direction other than parallel to the longitudinal axes of the linear drives. The longitudinal axes of the parallel drives also do not have to be parallel to one another, and the movements of the linear drives do not have to be synchronous, but may be offset somewhat cyclically. The cylinder may also be connected to the second drive parts other than by means of a bridge, for example by means of axles and joints. The load frame may be composed of any number of pieces or else be configured in one piece. It is basically also possible that the second driven drive parts of the drives are fixed in place with respect to that end of the sample region which faces it and the first drive parts are fixed in place with respect to the cylinder, instead of vice versa.

In addition, an emergency brake (for example, in the form of a shoe brake) may be provided for the cylinder, so that in the event of defects, a power failure or other unforeseen events an emergency brake brakes the cylinder and/or stops it in order to prevent damage to the sample and/or to the test apparatus.

The linear drives may also be cooled with water or other liquids, instead of with air, and this may sometimes result in an increase in power of up to 50% or more.

The sample region may also be shielded by means of suitable measures with respect to electromagnetic radiation and electromagnetic fields of the linear motors and/or other current-carrying and magnetic components of the test apparatus, in particular by means of metallic elements (layers, nets, etc.).

In particular, the bearings for cylinders and other parts, such as, for example, linear drive parts, etc., may be coated on a side facing the mounted element with a material having a low coefficient of friction (in particular PTFE), most advantageously a surface of this material which faces the mounted element being provided at least partially with grooves (in particular transversely to the direction of movement of the mounted element). These grooves can receive wear particles and/or abrasion and thereby prevent soiling of the bearing and of the mounted element or clogging of the interspace between the bearing and mounted element.

It is entirely irrelevant for the invention in which direction the cylinder and the linear drives move and whether the cylinder and/or linear drives are arranged above or below or laterally of the sample region (or in front of or behind it).

The housing may be composed of more or fewer parts than described above, in particular the front and rear housing plate may be formed in one part together with the housing cover. Any other divisions of the housing into any number of individual parts (also one-part housings) may be envisaged and are especially advantageous depending on the application. For example, housings composed of as few parts as possible have better sealing with respect, for example, to dust, water and the like, whereas multipart housings may advantageously facilitate access to the interior and, as a result, maintenance or repair. The housing may surround the test apparatus completely or only partially, and the sample region may also be surrounded completely, partially or not at all by the housing, depending on the application, if appropriate with an opening device in the housing for access to the sample region.

| List of Reference Symbols | |
|---|---|
| 1 | Test apparatus |
| 2 | Test set-up |
| 3 | Control unit |
| 4 | Computer |
| 5 | Sample |
| 10 | Automatic control system |
| 11.1-11.2 | Drive control |
| 20 | Load frame |
| 21 | Sample region |
| 22.1-22.2 | First drive part |
| 23.1-23.2 | Second drive part |
| 24 | Bridge |
| 25 | Cylinder |
| 26 | Cylinder end face |
| 27 | Adapter |
| 28 | Insert |
| 29 | Bearing module |
| 200 | Baseplate |
| 201 | Top plate |
| 202.1-202.2 | Side wall |
| 210 | Drive bed plate |
| 211 | Marked strip |
| 212.1-212.2 | Upper rubber buffer |
| 213.1-213.2 | Lower rubber buffer |
| 300.1-300.5 | Groove |
| 301.1-301.2 | Fastening plate |
| 400 | Front housing plate |
| 401.1-401.2 | Side housing |
| 402 | Housing cover |
| 601-603 | Beam |
| 604, 605 | Posts |
| 606 | Sample space |
| 607 | Free space |
| 608 | Cross member |
| 609, 610 | Bearing |
| 611 | Plunger |
| 612, 613 | Outsides |
| 614, 615 | Cylinder |
| 616, 617 | Piston |

The invention claimed is:

1. Test apparatus for the testing of a sample by mechanical action upon the sample, comprising:
   a) a sample region in a rigid and nonadjustable load frame which at least partially surrounds the sample region, and
   b) a cylinder, which is fastened to a bridge and is movable in relation to the sample region, c) a first and at least one further linear drive, each with a first drive part, which is connected firmly to the load frame and is fixed in place with respect to an end of the sample region which faces it, and with a second drive part, which is movable in relation to the first drive part and is driven and which is fixed in place with respect to the cylinder and can be moved downward and upward in relation to the sample region, d) the second drive parts being connected to one another by means of a bridge at their upper end remote from the sample region, e) the linear drives of the test apparatus being arranged in such a way that, when a second drive part of one linear drive is in a non-deflected initial position, all the other second drive parts of the other linear drives are also in their non-deflected initial position, characterized in that f) the cylinder extends from the bridge through the load frame, into the sample region, and g) the cylinder is guided in its movement by a bearing module which is part of the rigid load frame.

2. Test apparatus according to claim 1, characterized in that movement axes of the at least two linear drives run parallel to the longitudinal axis of the cylinder.

3. Test apparatus according to one of claims 1, characterized in that the second drive parts and the cylinder are connected to one another by means of at least one bridge, in particular the cylinder being connected rigidly to the bridge.

4. Test apparatus according to claim 1, characterized in that electromagnetic motors are used as the linear drive.

5. Test apparatus according to claim 1, characterized in that the linear drives are controlled individually by drive controls separate from one another, and in that the drive controls are controlled by a common automatic control system.

6. Test apparatus according to claim 1, characterized in that the longitudinal axis of the cylinder forms a rotational axis of symmetry for the longitudinal axes of the linear drives, wherein, in particular, in at least one section through the test apparatus running perpendicularly to the longitudinal axis of the cylinder, a straight line connecting all the points of penetration of the longitudinal axes of the linear drives through the sectional plane or an area spanning all the points of penetration of the longitudinal axes of the linear drives through the sectional plane has a geometric center of gravity which lies on a geometric center of gravity of the sectional area of the sample region through the sectional plane.

7. Test apparatus according to claim 1, characterized in that bearings for the cylinder are formed in a separate bearing module, the bearing module being configured as an exchangeable part of a load frame.

8. Test apparatus according to claim 1, characterized in that the cylinder is configured as a hollow profile, in particular as a circular-cylindrical hollow profile.

9. Test apparatus according to claim 1, characterized in that it comprises at least one measurement system which is coupled to the cylinder, in particular one or more of the following measurement systems: strain gages, position transmitters, force sensors for determining pressure force.

10. Test apparatus according to claim 1, characterized in that the cylinder and/or the margin of the sample region have/has quick-action fastenings.

11. Test apparatus according to claim 1, characterized in that an adapter is provided, and in that the cylinder or the adapter or both have fastening mechanisms in order to connect the cylinder and adapter nonpositively to one another, and/or in that inserts are provided which can be fastened to a margin of the sample region and, in particular, to a baseplate of a load frame at least partially surrounding the sample region and serve for positioning the sample in the sample region.

12. Test apparatus according to claim 1, characterized in that the linear drives are mounted laterally on the load frame.

13. Test apparatus according to claim 1, characterized in that two bearing modules are provided.

14. Test apparatus according to claim 1, characterized in that it is protected against damage and soiling by at least one housing, the at least one housing and, in particular, a housing in the vicinity of the sample region or delimiting the latter being designed to be at least partially dust-proof and watertight.

15. Test apparatus according to claim 1, characterized in that it comprises a test set-up in the form of a desk model.

16. Test method for the testing of samples by mechanical action upon the sample with a test apparatus according to claim 1, which comprises the following steps:

a) at least unidirectionally nonpositive connection of the sample to a margin of the sample region and b) at least unidirectionally nonpositive connection of the sample to a cylinder, characterized in that c) the deflection of the cylinder in relation to the sample region takes place as a result of the simultaneous movement of at least two linear drives.

17. Test apparatus according to claim 4, characterized in that servoelectric linear motors are used as the linear drive.

\* \* \* \* \*